(12) United States Patent
Okamoto et al.

(10) Patent No.: US 6,491,679 B1
(45) Date of Patent: Dec. 10, 2002

(54) SYSTEM FOR INFUSING INTRAVENOUS NUTRITION SOLUTIONS

(76) Inventors: Rodney Okamoto, 9127 Cape May Ct., Elk Grove, CA (US) 95758; Thomas G. Diamantidis, 17336 Napa St., Northridge, CA (US) 91325

(*) Notice: Subject to any disclaimer, the term of this patent is extended or adjusted under 35 U.S.C. 154(b) by 0 days.

(21) Appl. No.: 09/495,073

(22) Filed: Jan. 31, 2000

Related U.S. Application Data

(63) Continuation-in-part of application No. 08/954,437, filed on Oct. 20, 1997, now Pat. No. 6,071,262.

(51) Int. Cl.[7] .............................................. A61B 19/00
(52) U.S. Cl. ....................................................... 604/410
(58) Field of Search ................................. 604/267, 268, 604/408, 410, 411, 414, 416, 82, 85, 86, 87, 88

(56) References Cited

U.S. PATENT DOCUMENTS

| | | |
|---|---|---|
| 1,546,016 A | 7/1925 | Eisele |
| 3,788,374 A | 1/1974 | Saijo |
| 4,198,972 A | 4/1980 | Herb |
| 4,211,019 A | 7/1980 | McCafferty |
| 4,340,049 A | 7/1982 | Munsch .................. 128/214 R |
| 4,365,629 A | 12/1982 | Pert et al. |
| 4,396,383 A | 8/1983 | Hart |
| 4,410,321 A | 10/1983 | Pearson et al. |
| 4,458,811 A | 7/1984 | Wilkinson |
| 4,507,114 A | 3/1985 | Bohman et al. |
| 4,576,603 A | 3/1986 | Moss |
| 4,608,043 A | 8/1986 | Larkin |
| 4,611,643 A | 9/1986 | Beebe et al. ............. 141/311 R |
| 4,661,100 A | 4/1987 | Rechsteiner |
| 4,790,815 A | 12/1988 | Balteau et al. ................. 604/29 |
| 4,820,269 A * | 4/1989 | Riddell ........................ 604/85 |
| 4,863,454 A * | 9/1989 | Labove ........................ 604/416 |
| 4,997,083 A | 3/1991 | Loretti et al. |
| 5,180,504 A * | 1/1993 | Johnson et al. ............. 210/767 |
| 5,196,001 A * | 3/1993 | Kao ........................... 604/416 |
| 5,209,347 A | 5/1993 | Fabisiewicz et al. |
| 5,257,985 A | 11/1993 | Puhl |
| 5,330,464 A | 7/1994 | Mathias et al. ............. 604/415 |
| 5,394,907 A | 3/1995 | Hjertman et al. |
| 5,403,304 A * | 4/1995 | Ishida ........................ 604/403 |
| 5,560,403 A | 10/1996 | Balteau et al. |
| 5,562,836 A | 10/1996 | Joie et al. |
| 5,725,511 A * | 3/1998 | Urrutia ........................ 604/280 |

FOREIGN PATENT DOCUMENTS

| | | | |
|---|---|---|---|
| DE | 2433643 | 1/1976 | |
| EP | 0073847 | 9/1981 | ..................... 5/14 |

* cited by examiner

*Primary Examiner*—Manuel Mendez
(74) *Attorney, Agent, or Firm*—Coudert Brothers LLP (57) ABSTRACT

A containment and intravenous delivery bag device for supplying a patient with mixed chemical component nutrients includes a first pouch and a second pouch that are separated by a tube passageway. Using standard intravenous delivery bag sizes and manufacturing techniques, the tube passageway is blocked by either a clamp or a frangible valve fitted within the tube. The clamp or valve is opened, allowing fluids with the pouches to mix. The mixed liquid may then be delivered to the patient.

11 Claims, 6 Drawing Sheets

SYSTEM FOR INFUSING INTRAVENOUS NUTRITION SOLUTIONS

This application is a continuation-in-part of application Ser. No. 08/954,437 filed Oct. 20, 1997, now issued as U.S. Pat. No. 6,071,262, for "System for Infusing Intravenous Nutrition Solutions."

BACKGROUND OF THE INVENTION

1. Field of the Invention

A two-chambered receptacle for intravenous use is disclosed. Specifically, the subject receptacle comprises two pre-connected pouches linked by a connection tube that can be controlled to prevent mixing of the pouch components. More specifically, the two-chambered receptacle usually contains the components of a Total Parenteral Nutrition (TPN) solution. Usually, one pouch contains readily inactivated compounds such as lipids and the other pouch contains the remainder of the TPN solution.

2. Description of the Background Art

Complex solutions are often needed by patients undergoing varied types of medical treatments. Unfortunately, the components within the complex solutions often interact with one another when mixed. Thus, for reasons of chemical reactivity, neutralization, inactivation, precipitation, unwanted side-reactions, and the like, compartmented chemical, drug, and nutrient delivery containers need to exist and have existed for years. With these compartmented delivery systems, the components of the complex mixture are held in separate compartments, and the components are mixed immediately before usage by a patient.

Total Parenteral Nutrition (TPN) is one area in which complex mixtures of components are required. Typical components for a TPN solution are: fluids; carbohydrates; electrolytes; proteins; lipids; vitamins; and trace minerals. For diverse reasons, some patients can not be fed orally and require intravenous (IV) feeding. TPN supplies the nutrients needed by a particular patient. Usually, the nutrients are mixed by a pharmacy in a sterile IV container. Generally, the lipids should be separated from the bulk of the TPN solution until just prior to patient use. The subject invention permits such separation in an efficient, cost-effective, reliable, and easily-utilized form.

Various type of complex and costly medical solution bags have been presented in the previous literature. Most have numerous components that increase the expense of the product and augment the possibility of improper operation or wasted time in verifying that proper connections have been fashioned. One specific example of an existing two-chamber bag is one supplied by Baxter Laboratories (the All-In-One™). This bag is very similar to the one described in U.S. Pat. No. 4,458,811 referenced below, in that it contains two immediately adjacent chambers that are mixed by pulling away a "pull-tab" that separates the two chambers. Basically, a single bag is used with a rubber separator. Unfortunately, the type of arrangement with two immediately-related chambers has been found to leak during mixing and shipping (the rubber separator fails), a difficulty not found with the subject invention.

More specifically, U.S. Pat. No. 3,788,374 relates to a parenteral solution bag. Openings protrude from the perimeter of the bag for entering and exiting parenteral solution. A fused tearing tab is included with a protective closure for hermetically enclosing the protruding portion.

U.S. Pat. No. 4,198,972 discloses a blood and blood component storage bag having at least two hermetically-enclosed inlets at the top. Included is a burstable seal below at least one of the inlets.

Disclosed in U.S. Pat. No. 4,211,019 is an accommodative foot bed that has a resin storage bag that comprises two separated chambers with a jointly breakable connection. Upon breaking the connection, the resin components mix and enter a mixing chamber, thereby activating the resin for setting.

A platelet freezing bag is related in U.S. Pat. No. 4,365,629. Pull-apart seals protect as least two needle ports mounted in a flexible bag. An exit port is located near a push-apart seal formed in the body of the bag.

Described in U.S. Pat. No. 4,458,811 is a compartmented flexible solution container that has an elongated frangible member that separates the compartments. Breaking the elongated frangible member permits a user to mix the components kept within the compartments.

Presented in U.S. Pat. No. 4,507,114 is a multiple chamber container having a leak detection compartment. A leak detection pathway normally has no liquid within it, but upon leakage at the connection point between two compartments liquid appears in this leak detection pathway and a visual or similar detection system activated.

U.S. Pat. No. 4,608,043 describes an IV fluid storage and mixing system that has a two-compartment construction in which the two compartments are connected upon the application of force via a weakened section in a common wall. Once the weakened section ruptures, the solutions in each compartment encounter one another and mix when the bag is manipulated in a user's hand.

U.S. Pat. No. 4,661,100 discloses a urinary receptacle having a central bag for holding urine with least one internal container within the central bag that may be opened and the contents of the internal container mixed with the contents of the central bag.

Lastly, revealed in U.S. Pat. No. 5,394,907 is a device and method for dosing a liquid product. An enclosed bag has means for pinching off one or more compartments and means for introducing differing solutions into these pinched-off compartments. Upon removal of the pinching means, the solutions mix.

Each of the prior art inventions attempt to solve the problem of producing multi-chambered receptacles in ways that are not entirely satisfactory for IV use. For example, the prior art inventions often experience sealing problems that may cause or result in leaking between compartments. Other methods that incorporate mechanical separation do so in ways that are not entirely compatible with the size of IV equipment. In summary, there is a need in the art for improved multi-chambered IV receptacles.

The foregoing patents reflect the state of the art of which the applicant is aware, and are tendered with the view toward discharging applicant's acknowledged duty of candor in disclosing information which may be pertinent in the examination of this application. It is respectfully submitted, however, that none of these patents teach or render obvious, singly or when considered in combination, applicant's claimed invention.

SUMMARY OF THE INVENTION

An advantage of the present invention is to provide a liquid nutrient storage and delivery system that is leak-resistant and not subject to premature mixing of liquids contained within the system.

A further advantage of the present invention is to provide a method of utilizing a liquid nutrient storage and delivery system in a manner that minimizes leakage or inadvertent mixing of contained liquids.

Another advantage of the present invention is to disclose a liquid nutrient storage and delivery system that comprises relatively thin pouches that are approximately the same width as standard intravenous bags.

Yet another advantage of the present invention is to disclose a liquid nutrient storage and delivery system that contains two liquids that are stored separately from one another in the system prior to patient use, and allows for combining and mixing of the liquids prior to use.

An advantage of one embodiment of the present invention is to supply a liquid nutrient storage and delivery system that is leak-resistant and contains a connection tube that has a valve that permits mixing of two liquids only upon an irreversible breaking of a frangible member of the valve. As a further advantage, a liquid nutrient storage and delivery system is furnished that has two separate pouches connected by a valve-containing tube, thereby preventing leakage or mixing of liquids held within the pouches.

An advantage of a second embodiment of the present invention is to supply a liquid nutrient storage and delivery system that is leak-resistant and contains a connection tube with a clamp that permits mixing of the two liquids upon release of the clamp.

Yet a further advantage of the present invention is to provide a method of utilizing a liquid nutrient storage and delivery system in a manner that minimizes leakage or inadvertent mixing of contained liquids.

Disclosed is a containment and intravenous delivery system for supplying a patient with mixed chemical component nutrients. Comprising the subject invention is a first pouch usually having top, bottom, and two opposing side borders. More specifically, the first pouch additionally comprises a first port mounted in the first pouch bottom border and a second port mounted in the first pouch bottom border. The second port is for filling the first pouch with a first liquid.

Further included in the subject invention is a second pouch with about a standard intravenous single bag width. Like the first pouch, the second pouch has top, bottom, and two opposing side borders. The second pouch has a third port mounted proximate the second pouch top border, a fourth port mounted proximate the second pouch bottom border, a fifth port mounted proximate the second pouch bottom border, and a sixth port mounted proximate the second pouch bottom border.

In a first embodiment, a tube connects the first port and the third port and has a valve mounted in the tube. The valve comprises a body, a frangible element associated with the body, and a stop member. When the frangible element is broken, a first liquid within the first pouch may enter the second pouch through the tube and mix with a second liquid. The stop member prevents the frangible element from exiting the tube yet allows the first liquid to enter the second pouch through the tube.

Generally, the first embodiment incorporates additional means for releasably blocking the passageway at a position between the valve and the second pouch. Usually, the releasable blocking means comprises a ratchet, slide, on-off or some other type of clamp that fits about the tube and may be positioned between open and closed to allow liquid passage or to block liquid passage, respectively.

In a second embodiment, a tube connects the first port and the third port and has a blocking or clamping mechanism surrounding the tube. The clamping mechanism comprises a ratchet, slide, on-off or some other type of clamp to control the flow of material between pouches. Mixing of the first pouch contents in the second pouch occurs after the release of the clamping mechanism. Subsequent to clamp opening, the contents are mixed in the first pouch, and the clamp may be re-closed to keep the contents from flowing back into the second pouch.

One advantage of the subject TPN system over existing technologies is a much more effective separation of the two fluid components from one another, which minimizes leakage possibilities. Another advantage of the subject system is that the receptacle or pouches is much thinner than the existing bags (like the one found in the All-In-One™ system and equivalent structures). Thinness is important for the patient who must fit the bag into a backpack which is not designed for the wider-type bags. The wider design (like the one found in the All-In-One™ system) is to accommodate an adequate volume for the lipid chamber. The subject receptacle has a standard transfusion single bag width which patients, patient-producers, and patient-products have been using for several decades. Thus, the width of the subject system receptacle permits usage of standard-sized associated items. Additionally, some patients have been found to "fold" their wider bag systems (not the subject receptacle) to fit into their carrying cases. This can lead to a portion of the solution leaking into folds and crevices not readily accessible for delivery to the patient, and compromise the TPN therapy.

Other objects, advantages, and novel features of the present invention will become apparent from the detailed description that follows, when considered in conjunction with the associated drawings.

BRIEF DESCRIPTION OF THE DRAWINGS

FIG. 4C' is a top view and FIG. 4C" is a side cross-sectional view, with the clamp shown in a released (solid) and clamped (dashed) position.

DESCRIPTION OF THE PREFERRED EMBODIMENTS

Figure 1:
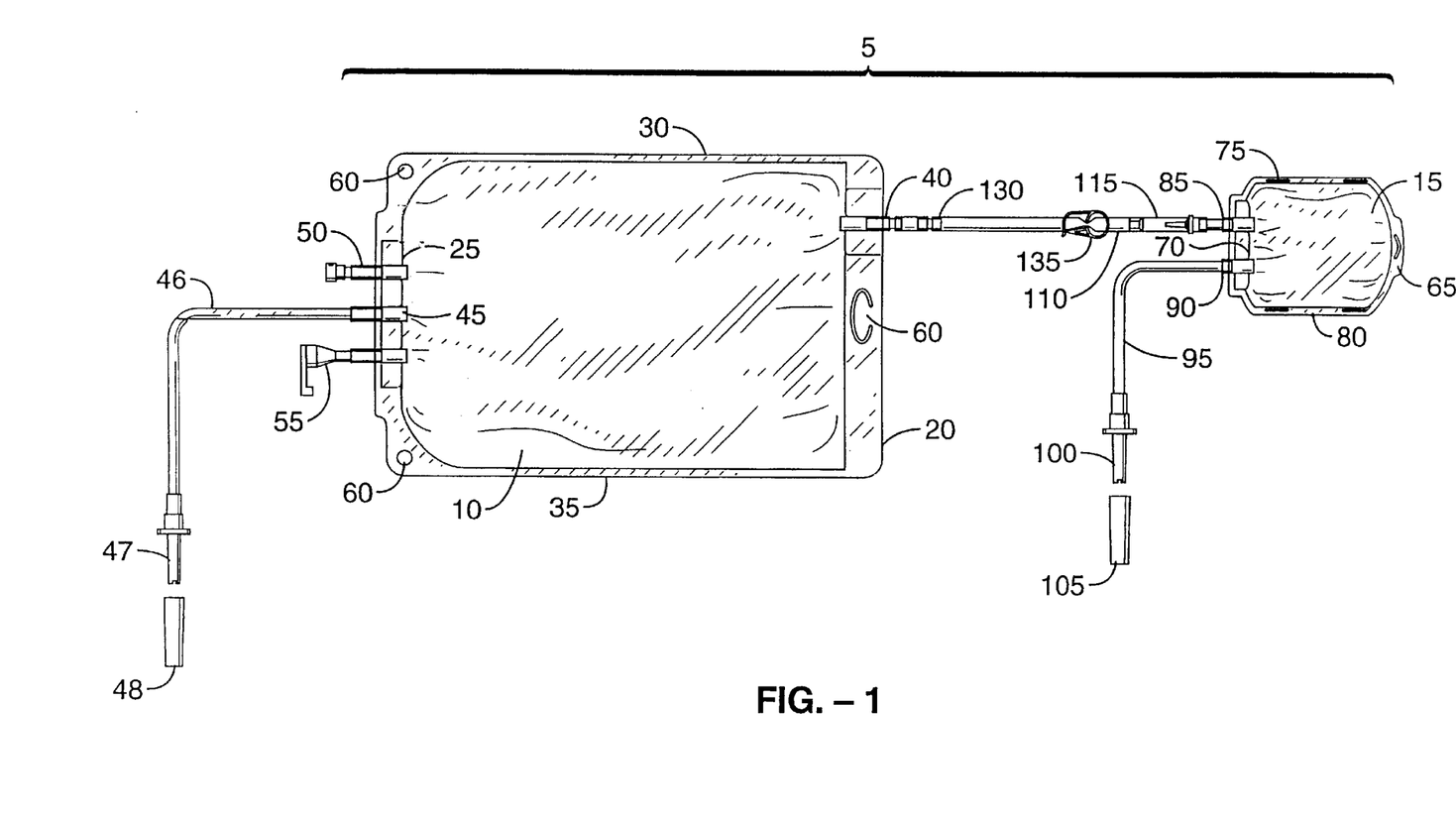
FIG. 1 is a planar view of a first embodiment of the subject invention.
Figure 2A:
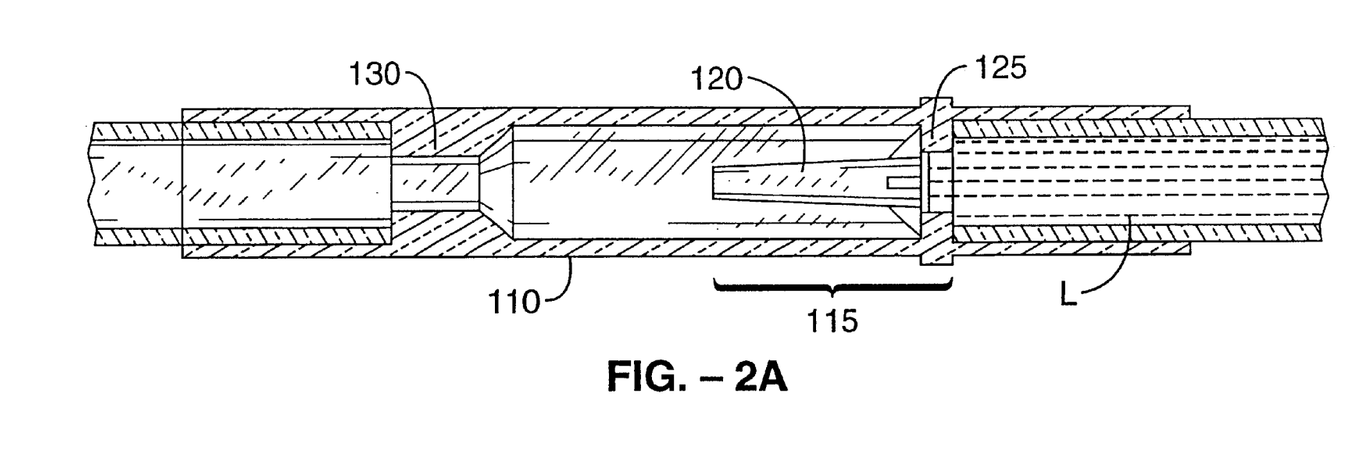
FIG. 2A is a cross-sectional elevational view of the "break-away" or frangible valve and associated tubing of the first embodiment of the subject invention showing no liquid flow within the tubing.
Figure 2B:
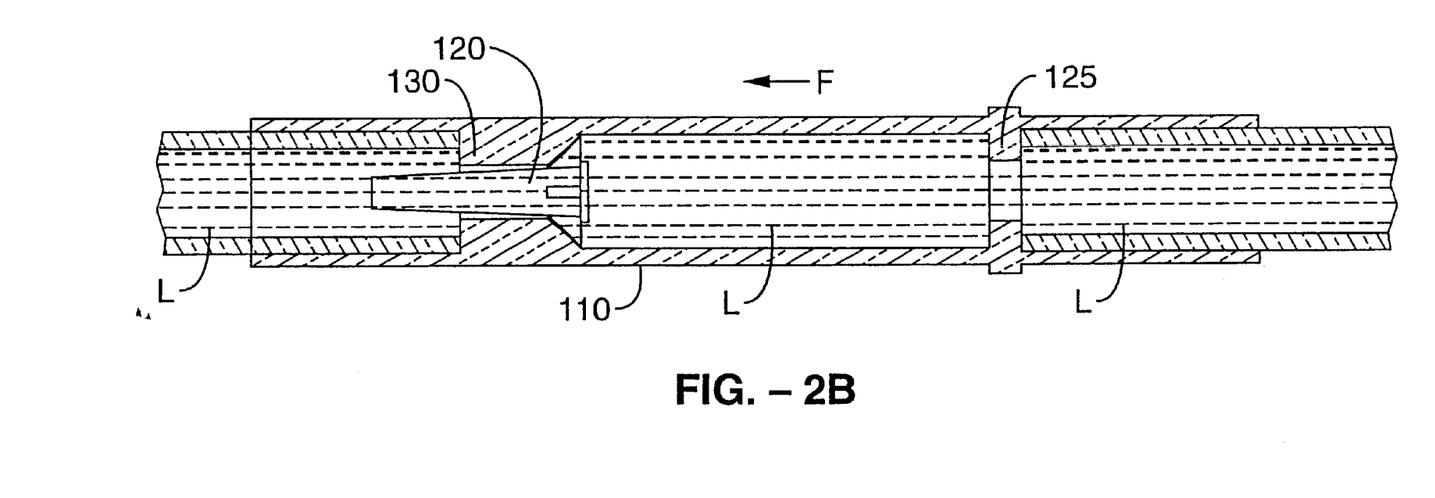
FIG. 2B is a cross-sectional elevational view of the "break-away" or frangible valve and associated tubing of the first embodiment of the subject invention showing free passage of a liquid through the tubing after the frangible valve is broken.

Referring now to FIGS. 1, 2A, and 2B, there is shown a first embodiment of a two-chambered nutrition bag or receptacle system 5. Comprising the subject system is a first or larger volume pouch or bag 10 and a second or smaller volume pouch or bag 15. Commonly, the larger pouch 10 holds between about one and about four liters, more generally about 2.5 liters. The smaller pouch 15 usually contains between about 50 mL and about one liter, more commonly about 300 mL. Each pouch 10 and 15 is fabricated from suitable natural and synthetic polymers, frequently ethylene vinyl acetate or equivalent material.

Although other equivalent configurations are within the realm of this disclosure, the larger pouch 10 generally comprises opposing polymeric sheets that are fused or adhered to one another to form the pouch 10. Preferably, the pouch 10 has top 20, bottom 25, and two opposing side borders 30 and 35. Ports are formed in the pouch 10 by standard means. Usually for the larger pouch 10, a port 40 is positioned proximate the top border 20 and is utilized in a liquid connection with the smaller pouch 15. Usually in the bottom border 25 of the larger pouch 10 is placed a fill port 45 used to fill the pouch 10 with the selected liquid nutrients or chemicals. A tube 46 connects to the fill port 45 and has associated with it a fill tip 47 and cover 48. Also, an injection port 50 is usually located in the bottom border 25, but other border locations are possible as would be with the fill port 45. The injection port 50 is employed to introduce additional components (chemicals, solutions, and the like) into the bulk solution within the pouch 10. Further, usually in the bottom border 25 is placed the patient port 55 that may be accessed by standard means for delivery of the contained liquid to the patient. Apertures 60 are formed in the pouch 10 for hanging the pouch in various desired positions.

As above with the larger pouch 10, although other equivalent configurations are within the realm of this disclosure, the smaller pouch 15 generally comprises opposing polymeric sheets that are fused or adhered to one another to form the pouch 15. Preferably, the pouch 15 has top 65, bottom 70, and two opposing side borders 75 and 80. Generally, a connection port 85 is placed in the bottom border 70 of the smaller pouch 15, as is a fill port 90. The fill port 90, like the fill port 45 for the larger pouch, is usually fitted with a tube 95, fill tip 100, and cover 105.

Connecting the two pouches 10 and 15 is a passage or tube 110 containing a valve 115 (see FIGS. 2A and 2B). Commonly, the tube 110 is fabricated from non-reactive natural or synthetic polymers such as TYGON™ tubing and the like. Although other frangible valve designs are within the realm of this invention, usually the valve 115 has a frangible element 120 and a base member 125. Without breaking the frangible element 120, no liquid L can flow (F in FIG. 2B) past the valve 115 which prevents leaks (see FIG. 2A). When the frangible element 120 is broken apart from the base member 125, liquid L may pass through the valve 115 and travel between the small pouch 15 and the larger pouch 10 (see FIG. 2B and the flow arrow associated with notation F). The frangible element 120 generally separates from the base member 125 and is prevented from migrating in the tube 110 by a stop 130 fitted within the tube 110. Liquid L is able to flow F through the stop 130 and the stop only inhibits the motion of the frangible element 120.

Usually, the tube 110 is fitted with a releasable blocking means such as a ratchet clamp 135. This clamp 135 serves as a means for preventing flow back into the smaller pouch 15 after mixing and as a secondary means for preventing leakage between the two pouches 10 and 15 before a desired mixing.

Often the subject system is used by placing lipid in the smaller pouch 15 via fill spike 100 and the TPN solution in the larger pouch 10 via fill spike 47. Frequently, the fill ports 45 and 90 are sealed and the tubes 46 and 95 are removed before the subject system is shipped to a user. The breakaway valve 115 and the ratchet clamp 135 ensure that the two solutions do not mix during shipping and storage.

Just prior to hookup by a selected patient, the patient opens the ratchet clamp 130 and breaks the frangible member 120 from the base member 125 by bending the tubing 110 at the valve 115 until the lipids can freely flow into the larger pouch 10. Generally, the ratchet clamp 135 is closed after the lipids are mixed into the larger pouch 10 to prevent back-flow of the mixed liquid into the smaller pouch 15 and the patient can then access the final solution via the patient port 55.

Figure 3:
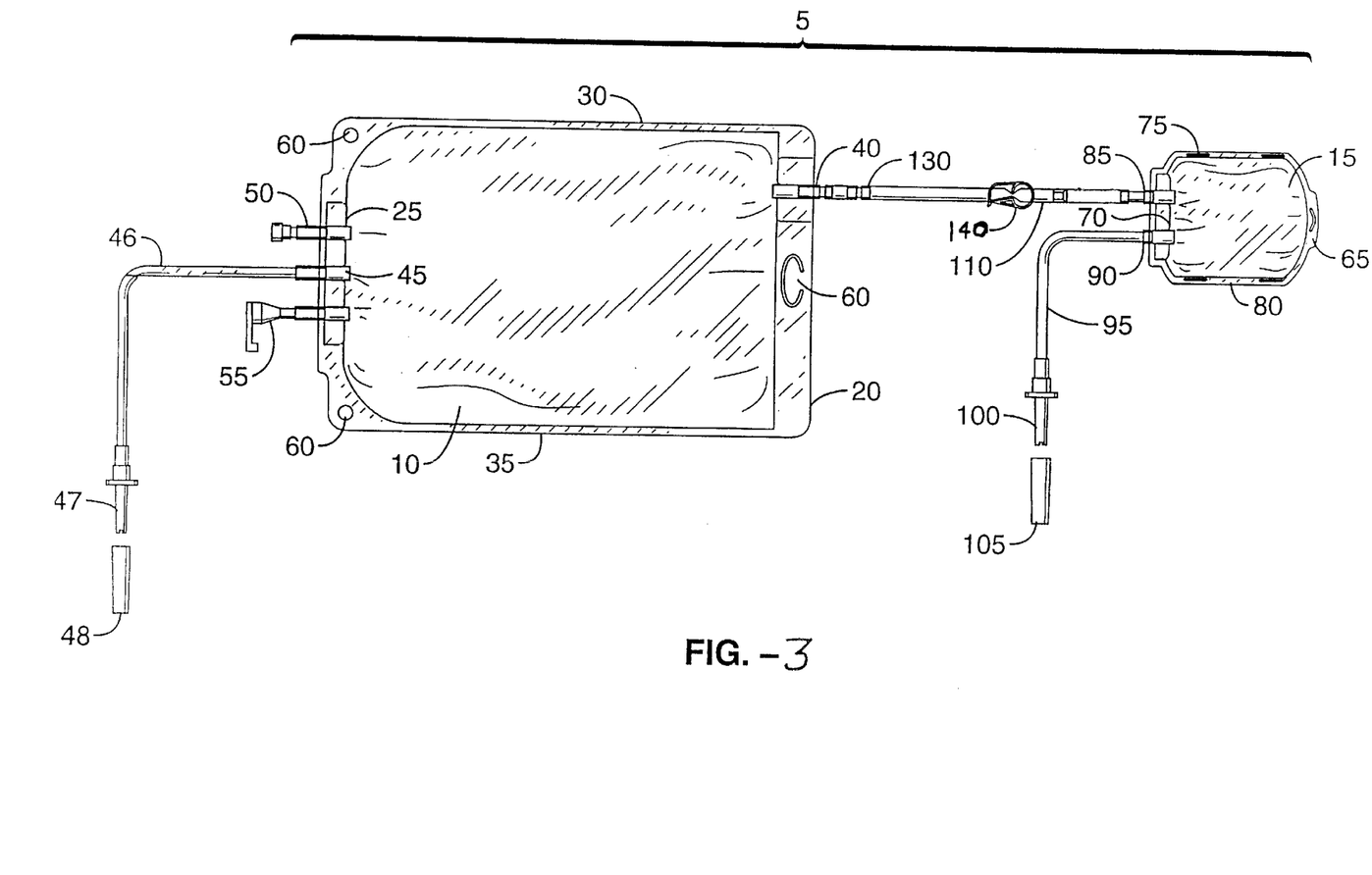
FIG. 3 is a planar view of a second embodiment of the subject invention.
Figure 4A:
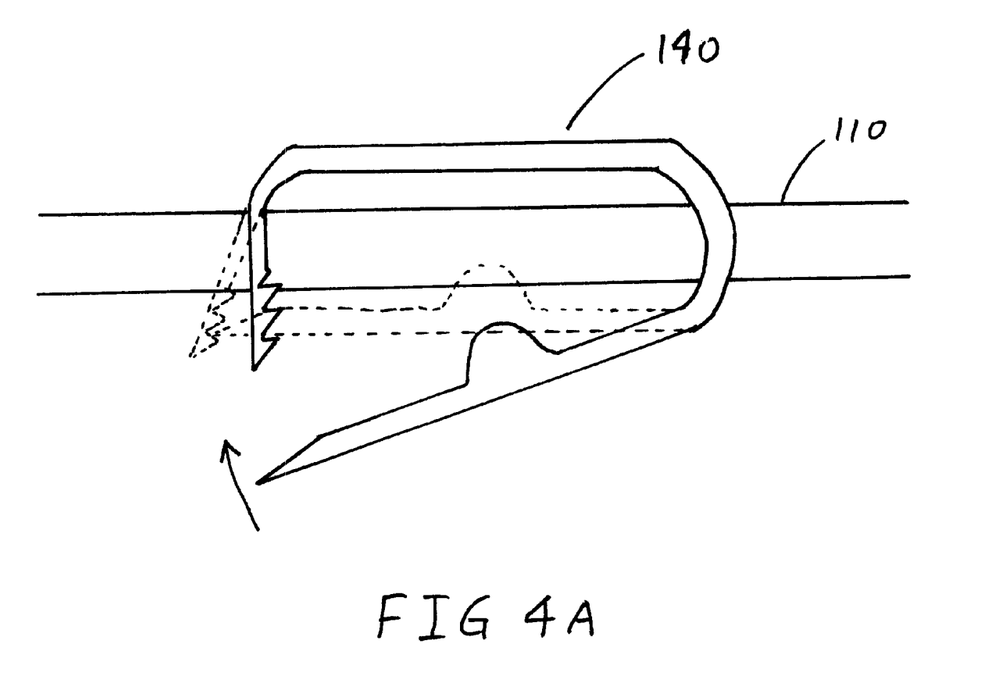
FIG. 4A is a side view of the ratchet clamp comprising the clamp assembly of the second embodiment. The clamp is shown in a released (solid) and clamped (dashed) position.
Figure 4B:
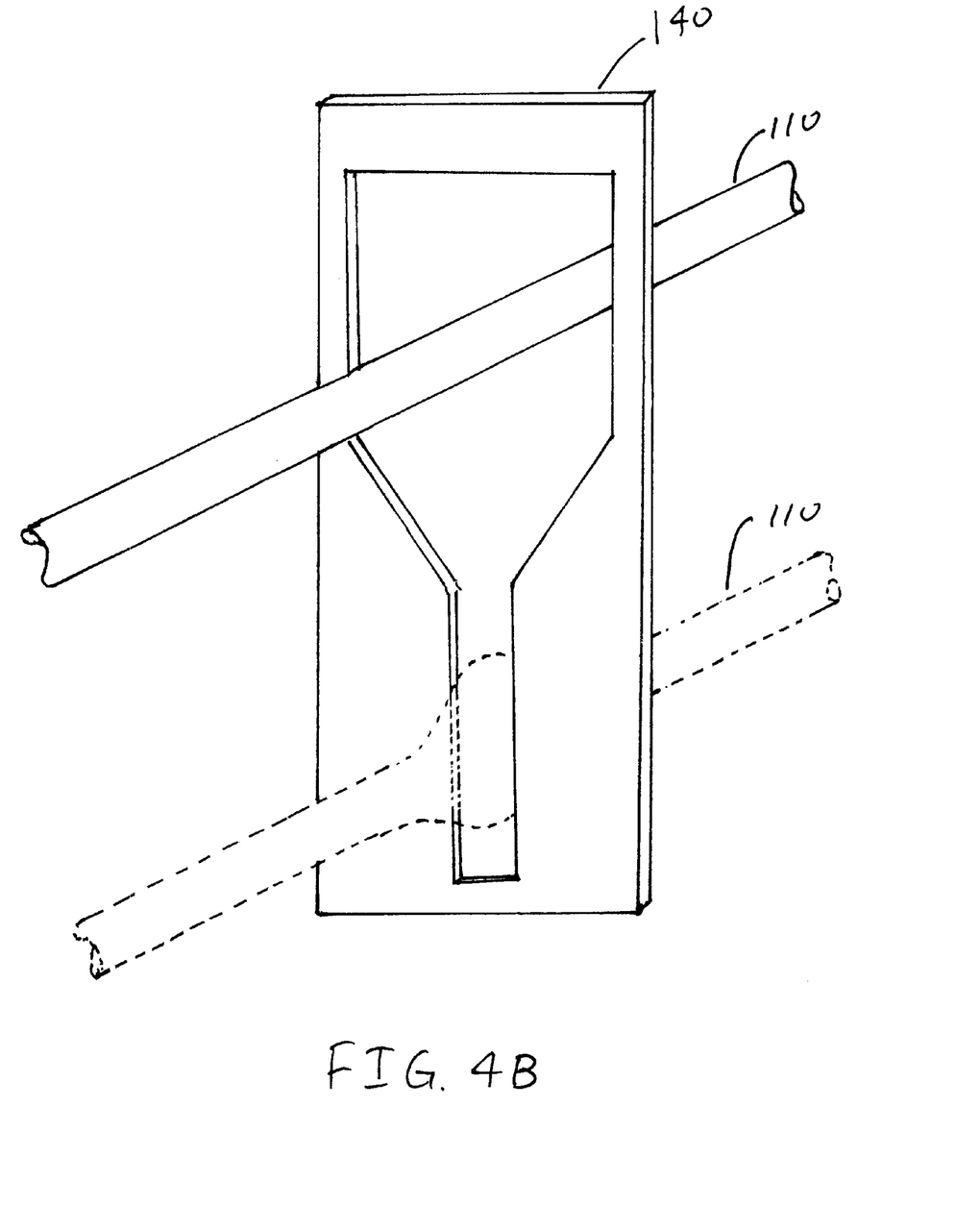
FIG. 4B is a perspective view of the slide clamp comprising the clamp assembly of the second embodiment. Tubes are shown in a released (solid) and clamped (dashed) position.
Figure 4C:
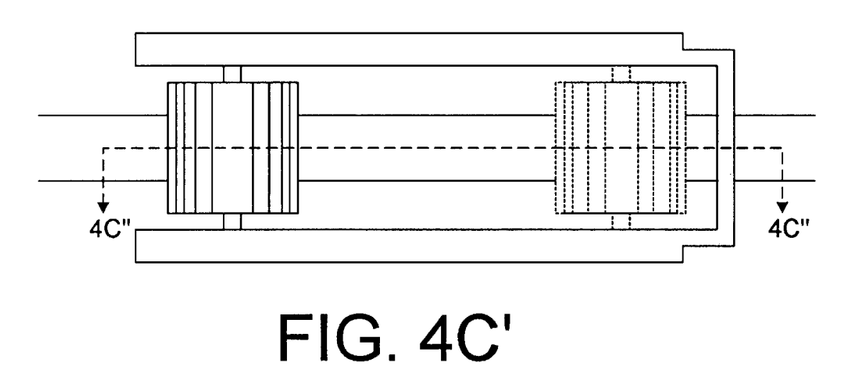
FIG. 4C is a view of the on-off clamp comprising the clamp assembly of the second embodiment.

Referring now to FIGS. 3 and 4A–C, there is shown a second embodiment of a two-chambered nutrition bag or receptacle system 5. The configuration and limitations of each of pouches 10 and 15 are the same as those described for the first embodiment, including materials and construction. In the second embodiment, tube 110 is fitted with clamp 140 to prevent the flow of liquid between pouches 10 and 15 in place of valve 115 of the first embodiment (see FIG. 1). Clamp 140 ensures that the two solutions do not mix during shipping and storage, and also serves as the means for preventing flow back into the smaller pouch 15 after mixing. The function of clamp 140 is to isolate the contents of pouches 10 and 15 before mixing of the liquids in pouch 10, and keeping the mixed liquids from flowing back into pouch 15 after mixing. Examples of three of the many type of clamps that can perform this function are the ratchet clamp, slide clamp and on-off clamp, as shown in FIGS. 4A–C respectively. Clamped and unclamped positions are shown for each of the clamps on FIG. 4 using dashed and solid lines, respectively. In a first clamp embodiment, FIG. 4A shows clamp 140 as a ratchet clamp in side view, with both the unclamped (solid) and clamped (dashed) configurations illustrated. A second clamp embodiment is shown in FIG. 4B, where clamp 140 is a slide clamp in perspective view. Tube 110 is shown relative to the clamp in an unclamped position (solid) and clamped position (dashed). A third clamp embodiment is shown in FIG. 4C. FIG. 4C' is a top view and FIG. 4C" is a side cross-sectional view of an on-off clamp 140. The clamp is shown in an unclamped (solid) and clamped (dashed) configuration. Each of the three clamp embodiments can reversibly stop and start the flow through tube 110. The description of clamp types and clamp operation described and shown herein is not meant to limit the scope of this invention. In particular, there are many other clamp types and configurations known to those in the art, in addition to the embodiments described here, that could perform the functions of clamp 140, and should be considered to be equivalent.

One of the many possible modes of operation of the second embodiment is illustrated in the previously-considered example of placing lipid in the smaller pouch 15 via fill spike 100 and the TPN solution in the larger pouch 10 via fill spike 47. Frequently, the fill ports 45 and 90 are sealed and the tubes 46 and 95 are removed before the subject system is shipped to a user. The clamp 140 ensures that the two solutions do not mix during shipping and storage.

Just prior to hookup by a selected patient, the patient opens clamp 140, allowing the lipids to freely flow into the larger pouch 10. Generally, the clamp 140 is closed after the lipids are mixed into the larger pouch 10 to prevent back-flow of the mixed liquid into the smaller pouch 15 and the patient can then access the final solution via the patient port 55.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A containment and intravenous delivery system for supplying a patient with mixed chemical component nutrients, comprising:
   (a) a first pouch containing a first liquid;
   (b) a second pouch containing a second liquid;
   (c) a first tube connected to said first and second pouches;
   (d) a clamp adapted to releasably pinch said first tube for controlling the flow of said liquids between said pouches, said clamp positions including:
      (i) a first position where the clamp does not pinch said first tube closed, allowing said liquids to flow between said pouches, and
      (ii) a second position where the clamp pinches said first tube closed, blocking said liquids from flowing between said pouches; and
   (e) a second tube connected to said second pouch for delivering contents from said second pouch to the patient.

2. A containment and intravenous delivery system according to claim 1 wherein said first pouch further comprises means for filling with said first liquid.

3. A containment and intravenous delivery system according to claim 1 wherein said second pouch further comprises:
   (a) means for filling with said second liquid; and
   (b) means for accessing said second pouch for introducing additional chemical components.

4. A containment and intravenous delivery system according to claim 1 wherein the clamp is a ratchet clamp.

5. A containment and intravenous delivery system according to claim 1 wherein the clamp is a slide clamp.

6. A containment and intravenous delivery system according to claim 1 wherein the clamp is an on-off clamp.

7. A containment and intravenous delivery system for supplying a patient with mixed chemical component nutrients, comprising:
   (a) a first pouch having top, bottom, and two opposing side borders, comprising:
      (i) a first connection port mounted in said first pouch bottom border; and
      (ii) a first fill port mounted in said first pouch bottom border, wherein said first fill port is for filling said first pouch with a first liquid;
   (b) a second pouch with about a standard intravenous single bag width having top, bottom, and two opposing side borders, comprising:
      (i) a second connection port mounted proximate said second pouch top border;
      (ii) a second fill port mounted proximate said second pouch bottom border;
      (iii) an injection port mounted proximate said second pouch bottom border; and
      (iv) a patient port mounted proximate said second pouch bottom border;
   (c) a tube connected to said first connection port and said second connection port; and
   (d) a clamp adapted to releasably pinch said tube, said clamp having at least two positions for controlling the flow of said liquids between said pouches, and where said clamp positions include:
      (i) an unpinched position where the clamp does not pinch the tube closed, allowing said liquids to flow between said pouches, and
      (ii) a pinched position where the clamp pinches the tube closed, blocking the flow of said liquids between said pouches.

8. A containment and intravenous delivery system according to claim 7 wherein the clamp is a ratchet clamp.

9. A containment and intravenous delivery system according to claim 7 wherein the clamp is a slide clamp.

10. A containment and intravenous delivery system according to claim 7 wherein the clamp is an on-off clamp.

11. A method of infusing a mixture of nutrients to a patient using a two separate pouches combination, said two separate pouches combination comprising a first pouch and a second pouch, wherein said first pouch contains a first liquid, and said second pouch contains a second liquid, wherein said first pouch and said second pouches are connected by a releasably pinchable tube having a clamp for controlling the flow and mixing of said liquids between said pouches, comprising the steps of:
   (a) filling said first pouch with said first liquid through a first fill port;
   (b) filling said second pouch with said second liquid through a second fill port;
   (c) sealing said first fill port;
   (d) sealing said second fill port;
   (e) providing said two pouches combination to the patient;
   (f) opening the clamp so that said first liquid within said first pouch may enter said second pouch through said tube and mix with said second liquid; and
   (g) infusing the mixture of said first liquid and said second liquid from said second pouch to the patient.

* * * * *